United States Patent [19]

Brown et al.

[11] Patent Number: 4,480,132

[45] Date of Patent: Oct. 30, 1984

[54] PROCESS FOR THE PREPARATION OF α,β-UNSATURATED KETONES

[75] Inventors: William T. Brown, Johnson City; Robert M. Simons, Kingsport, both of Tenn.

[73] Assignee: Eastman Kodak Company, Rochester, N.Y.

[21] Appl. No.: 553,930

[22] Filed: Nov. 21, 1983

[51] Int. Cl.$^3$ .............................. C07C 45/60
[52] U.S. Cl. ........................ 568/42; 568/43; 568/314; 568/338; 568/386; 568/390; 502/226; 502/227; 502/229; 502/231; 549/78; 549/498
[58] Field of Search ............. 568/41, 42, 386, 390, 568/43, 314, 338; 502/226, 227, 229, 231; 549/274, 78, 498

[56] References Cited

U.S. PATENT DOCUMENTS

| | | | |
|---|---|---|---|
| 2,108,427 | 2/1938 | Boese | 568/391 |
| 3,024,249 | 3/1962 | Wöllner | 568/390 |
| 3,989,737 | 11/1976 | Sawaki et al. | 71/88 |
| 4,059,634 | 11/1977 | Smith, Jr. | 568/386 |
| 4,249,937 | 2/1981 | Iwataki et al. | 71/97 |
| 4,355,184 | 10/1982 | Kaku et al. | 568/397 |

FOREIGN PATENT DOCUMENTS

| | | | |
|---|---|---|---|
| 1052385 | 3/1959 | Fed. Rep. of Germany | 568/386 |
| 430683 | 4/1924 | German Democratic Rep. | 568/390 |

OTHER PUBLICATIONS

Hurd et al., *J. Am. Chem. Soc.*, 61, 3355, (1939).
Carroll et al., *J. Am. Chem. Soc.*, 74, 6305, (1952).

*Primary Examiner*—Natalie Trousof
*Assistant Examiner*—Bruce D. Gray
*Attorney, Agent, or Firm*—J. Frederick Thomsen; Daniel B. Reece, III

[57] ABSTRACT

Disclosed is a process for the preparation of α,β-unsaturated ketones containing a 2-oxopropylidene moiety by the reaction of an aldehyde with a 2,2-dialkyl-4-methyl-6-keto-1,3-dioxene in the presence of a catalytic amount of certain metallic halides.

7 Claims, No Drawings

PROCESS FOR THE PREPARATION OF α,β-UNSATURATED KETONES

DESCRIPTION

This invention relates to a novel process for the preparation of certain α,β-unsaturated ketones by the reaction of an aldehyde with a 2,2-dialkyl-4-methyl-6-keto-1,3-dioxene in the presence of a catalytic amount of certain metallic halides.

The preparation of α,β-unsaturated ketones by the reaction of aldehydes and diketene at elevated temperature has been described by A. B. Boese in U.S. Pat. No. 2,108,427 and *Ind. Eng. Chem.*, 32, 16 (1940) and by C. D. Hurd and A. S. Roe in *J. Am. Chem. Soc.*, 61, 3355 (1939). Other procedures for the synthesis of α,β-unsaturated ketones are described in U.S. Pat. No. 4,355,184 and in the references cited therein.

We have discovered that certain α,β-unsaturated ketones can be obtained in acceptable yields with a minimum of process steps by reacting an aldehyde with a 2,2-dialkyl-4-methyl-6-keto-1,3-dioxene (or 2,2-dialkyl-6-methyl-4H-1,3-dioxin-4-one; DMKD) at elevated temperature in the presence of a catalytic amount of certain metallic halides. The compounds provided by our novel process are characterized by a 2-oxopropylidene moiety derived from the DMKD reactant with the remainder of the compound consisting of the residue of the aldehyde reactant, e.g.

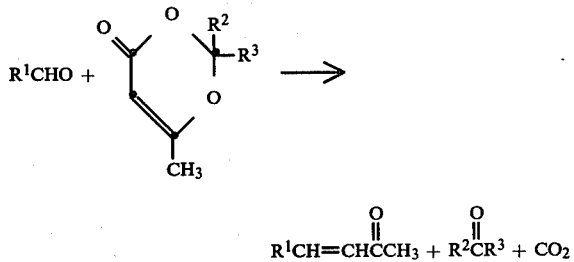

$$R^1CH=CHCCH_3 + R^2CR^3 + CO_2$$

wherein $R^1CH$ is the residue of the aldehyde reactant and $R^2$ and $R^3$ each is alkyl.

The DMKD reactants can be prepared according to the procedures described in *J. Am. Chem. Soc.*, 74, 6305 (1952) and 75, 5400 (1953) or by procedures analogous thereto. Although 2,2,4-trimethyl-6-keto-1,3-dioxene (TKD) has been used as a stable alternative to diketene in many reactions, the reaction thereof with 3-ethylthiobutanal in the absence of a catalyst gives 2,4-dimethyl-2-(2-ethylthiopropyl)-6-keto-1,3-dioxene rather than the desired α,β-unsaturated ketone. This adduct is not converted to the desired product upon heating it in the presence of the metallic halide catalysts useful in our novel process.

Examples of the aldehydes which may be used in and the products obtainable from our process are set forth in the references cited hereinabove, particularly U.S. Pat. No. 4,355,184. Generally, any aldehyde may be used provided it does not contain any substituents, such as amino or hydroxy, which are reactive with TKD or would otherwise alter the course of the reaction. Typical residues which $R^1$ may represent are alkyl of up to about 12 carbon atoms including substituted alkyl such as lower (up to about 4 carbon atoms) alkylthioalkyl; cycloalkyl such as cyclohexyl and lower alkylcyclohexyl; aryl such as phenyl and phenyl substituted with lower alkyl, lower alkoxy and/or halogen; styryl; and heterocyclic groups such as furyl and thienyl. Particularly preferred aldehyde reactants and 2-oxopropylidene products are those wherein $R^1$ is a residue having the formula $R^4$-S-A- wherein $R^4$ is lower alkyl, preferably ethyl, and A is lower alkylene, preferably propylene $[CH(CH_3)CH_2]$.

The groups represented by $R^2$ and $R^3$ are residues of the aliphatic or cycloaliphatic ketone from which the DMKD reactant is derived. These groups may be the same or different alkyl groups containing, for example, up to about six carbon atoms. Alternatively, $R^2$ and $R^3$ may collectively represent an alkylene group such as pentamethylene and hexamethylene. The preferred DMKD reactant is 2,2,4-trimethyl-6-keto-1,3-dioxene (TKD). The mole ratio of DMKD to aldehyde typically may be in the range of at least 1.0 and not more than 2.0 although ratios of about 1.05 to 1.1 give the best results.

The 2-oxopropylidene compounds obtained in accordance with our novel process are useful intermediates for synthesizing a wide variety of compounds such as the herbicides described in U.S. Pat. Nos. 3,989,737 and 4,249,937 and U.K. patent application No. 2,090,246.

The catalysts we have found to be useful in our novel process include the halides of aluminum, cobalt, iron, manganese, nickel, tin, titanium and zinc, particularly the chlorides of such metals and their hydrates. The chlorides of aluminum and titanium have been found to give relatively poor yields of 2-oxopropylidene product and accordingly are not preferred. Examples of the catalysts which give moderate to good results are cobaltous chloride ($CoCl_2$, $CoCl_2.6H_2O$), ferric chloride ($FeCl_3$, $FeCl_3.2H_2O$, $FeCl_3.6H_2O$), manganous chloride ($MnCl_2$, $MnCl_2.4H_2O$), nickel chloride ($NiCl_2$, $NiCl_2.6H_2O$), stannous chloride ($SnCl_2$, $SnCl_2.H_2O$), stannic chloride ($SnCl_4$) and zinc chloride ($ZnCl_2$). The most effective catalysts are the chlorides of zinc and tin. The chlorides of tin are especially preferred because of their selectivity which permits the use of higher temperatures and substantially shorter reaction times without sacrificing yields of product.

The amount of catalyst that may be employed will vary considerably depending on such factors as the particular metallic halide being used, reaction conditions and the conversion-yield desired. Typically, the catalyst will be used in a concentration of at least 0.01 mole percent and not more than 5.0 mole percent based on the amount of aldehyde reactant present. The preferred tin catalysts give the best results when used in a concentration of about 0.03 to 0.05 mole percent.

The temperatures at which our process may be carried out are in the range of about 60° to 110° C. although temperatures near the lower point of the range may require unduly long reaction times and temperatures near the upper limit can cause the formation of impurities affecting the quality of the 2-oxopropylidene product. The reaction temperature which gives optimum results will vary depending primarily upon the catalyst being used. For example, we have found that best results are obtained from zinc chloride-catalyzed reactions that are carried out at a temperature in the range of about 70° to 80° C. whereas when a tin chloride is the catalyst best results are obtained at a temperature in the range of about 90° to 95° C. An inert solvent such as an aliphatic or aromatic hydrocarbon or a chlorinated aliphatic or aromatic hydrocarbon having a boiling point of at least 60° C. may be employed in the process although the presence of a solvent is neither necessary nor preferred. The yields of product obtained from the process are decreased significantly by the presence of water and thus best results are accomplished when the process is carried out under essentially anhydrous conditions.

Our invention is further illustrated by the following examples.

EXAMPLE 1

Into a 5 liter flask were charged 1320 g of 3-ethylthiobutanal, 1562 g of TKD, and 13.6 g of anhydrous zinc chloride. The solution was heated with agitation under a nitrogen atmosphere at 75° C. for 23 hours. The yield of 6-ethylthio-3-hepten-2-one in the crude product mixture, as determined by gas liquid chromatography (GLC) using a known standard of the product, is 64.4%. The product may be used as described in U.S. Pat. No. 4,249,937 without isolating it or treating the final reaction mixture further.

EXAMPLES 2–10

The procedures of Example 1 was repeated using varying temperatures, amounts of zinc chloride and/or amounts of TKD. Reaction times were 23 hours except in Examples 5 and 10 in which the time of reaction was six hours. The following table sets forth the temperature (°C.), the concentration of zinc chloride (mole percent based on the aldehyde) and the amount of TKD (expressed as a mole percent excess based on the aldehyde reactant) used in each example. The conversion and yield values refer respectively to the percent of aldehyde reactant consumed and the percent of aldehyde consumed that is converted to 6-ethylthio-3-hepten-2-one.

TABLE

| Example | Temp. | ZnCl$_2$ | TKD | Conversion | Yield |
|---|---|---|---|---|---|
| 2 | 65 | 0.3 | 0* | 57 | 70 |
| 3 | 85 | 0.3 | 0 | 98 | 65 |
| 4 | 65 | 3.0 | 0 | 78 | 62 |
| 5 | 85 | 3.0 | 0 | 97 | 64 |
| 6 | 65 | 0.3 | 25 | 61 | 81 |
| 7 | 85 | 0.3 | 25 | 96 | 47 |
| 8 | 65 | 3.0 | 25 | 89 | 64 |
| 9 | 85 | 3.0 | 25 | 100 | 63 |
| 10 | 75 | 1.0 | 10 | 99 | 71 |

*TKD: aldehyde mole ratio = 1.0.

EXAMPLE 11

A mixture of 1.5 g TKD, 1.3 g 3-ethylthiobutanal and 0.15 g ferric chloride (FeCl$_3$.2H$_2$O) was heated with stirring at 60°–70° C. for three hours. A sample of crude product isolated by thin layer chromatography was found by NMR analysis to contain primarily 6-ethylthio-3-hepten-2-one.

EXAMPLE 12

A mixture of 5.98 g of 2,2-diethyl-4-methyl-6-keto-1,3-dioxene, 2.64 g 3-ethylthiobutanal and 0.1 g zinc chloride was stirred under a nitrogen atmosphere at 70°–75° C. for two hours and then at 80°–85° C. for three hours. About 0.5 g of the reaction mixture was fractionated by column chromatography. NMR analysis indicated that the first of two fractions obtained consisted of 6-ethylthio-3-hepten-2-one.

EXAMPLE 13

A mixture of 2.1 g of the diketene-cyclohexanone adduct having the formula

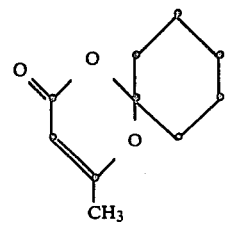

1.3 Grams 3-ethylthiobutanal and 0.15 zinc chloride were heated with stirring at 65°–75° C. under an argon blanket for 18 hours. The presence of the desired product, 6-ethylthio-3-hepten-2-one, in the reaction mixture was indicated by thin layer chromatography.

EXAMPLE 14

A mixture of about 2.0 g TKD, 1.3 g butyraldehyde and 0.15 g zinc chloride was heated with stirring at 75° C. for three hours. Thin layer chromatography established that the crude product consisted essentially of one compound which NMR confirmed to be 3-hepten-2-one.

EXAMPLE 15

A mixture of 13.2 g 3-ethylthiobutanal, 15.6 g TKD and 0.05 g FeCl$_3$ was heated at 75° C. with stirring under nitrogen for 23 hours. This reaction resulted in complete conversion of the 3-ethylthiobutanal with a 46.3% yield (as determined by GLC) of 6-thioethyl-3-hepten-2-one.

EXAMPLE 16

A mixture of 13.2 g 3-ethylthiobutanal, 15.6 g TKD and 0.01 g FeCl$_3$ (added as 1 ml of a 1% FeCl$_3$-acetone solution) was heated at 75° C. with stirring under nitrogen for 23 hours. The conversion of 3-ethylthiobutanal to products was 97.7%, and the yield of 6-thioethyl-3-hepten-2-one was 58.6%.

EXAMPLE 17

A mixture of 13.2 g 3-ethylthiobutanal, 15.6 g TKD and 0.2 g MnCl$_2$.4H$_2$O was held at 75° C. with stirring under nitrogen for 6.5 hours. The conversion of 3-ethylthiobutanal was 66%, and the yield of 6-thioethyl-3-hepten-2-one based on aldehyde converted was 49.4%.

EXAMPLE 18

A mixture of 13.2 g 3-ethylthiobutanal, 15.6 g TKD and 0.24 g NiCl$_2$.6H$_2$O was held at 75° C. with stirring under nitrogen for seven hours. The conversion of 3-ethylthiobutanal was 66%, and the yield of 6-thioethyl-3-hepten-2-one based on aldehyde converted was 40%.

EXAMPLE 19

A mixture of 13.2 g 3-ethylthiobutanal, 15.6 g TKD and 0.05 g CoCl$_2$.6H$_2$O was held at 75° C. with stirring under nitrogen for 19.5 hours. The conversion of 3-ethylthiobutanal to products was 96.2%, and the yield of 6-thioethyl-3-hepten-2-one based on aldehyde converted was 58.5%.

EXAMPLE 20

A mixture of 13.2 g 3-ethylthiobutanal, 15.6 g TKD and 0.01 g CoCl$_2$ was held at 85° C. with stirring under nitrogen for 7.5 hours. The resulting reaction mixture contained no starting material. The yield of 6-thioethyl-3-hepten-2-one was 51.2% as determined by GLC analysis.

EXAMPLE 21

A mixture of 13.2 g 3-ethylthiobutanal, 15.6 g TKD and 0.005 ml SnCl$_4$ was held at 85° C. with stirring under nitrogen for 7.5 hours. The conversion of the aldehyde reactant was 97%, and the yield of 6-thioethyl-3-hepten-2-one was 68% based on the aldehyde converted.

EXAMPLE 22

A mixture of 13.2 g 3-ethylthiobutanal, 15.6 g TKD and 0.01 g SnCl$_2$.2H$_2$O was held at 90° C. for six hours under nitrogen with stirring. The conversion of the 3-ethylthiobutanal was 98%, and the yield of 6-thioethyl-3-hepten-2-one was 71%.

EXAMPLE 23

A mixture of 13.2 g 3-ethylthiobutanal, 15.6 g TKD and 0.01 g anhydrous SnCl$_2$ was held at 90° C. for five hours with stirring under nitrogen. The conversion of the aldehyde reactant was 99%, and the yield of 6-thioethyl-3-hepten-2-one was 75% as determined by GLC analysis.

The invention has been described in detail with particular reference to preferred embodiments thereof, but it will be understood that variations and modifications can be effected within the spirit and scope of the invention.

We claim:

1. Process for the preparation of a 2-oxopropylidene compound which comprises reacting an aldehyde with a 2,2-dialkyl-4-methyl-6-keto-1,3-dioxene in the presence of a catalytic amount of a halide of aluminum, cobalt, iron, manganese, nickel, tin, titanium or zinc.

2. Process according to claim 1 which comprises reacting an aldehyde with a 2,2-dialkyl-4-methyl-6-keto-1,3-dioxene in the presence of a catalytic amount of a chloride of cobalt, iron, manganese, nickel, tin or zinc.

3. Process according to claim 1 which comprises reacting an aldehyde with a 2,2-dialkyl-4-methyl-6-keto-1,3-dioxene in the presence of a catalytic amount of a chloride of tin or zinc.

4. Process according to claim 1 wherein the process is carried out at a temperature of about 60° to 110° C. in the presence of about 0.01 to 5.0 mole percent of a catalytic amount of a chloride of cobalt, iron, manganese, nickel, tin or zinc.

5. Process for the preparation of a 2-oxopropylidene compound having the formula

which comprises reacting an aldehyde having the formula R$^4$-S-A-CHO with 2,2,4-trimethyl-6-keto-1,3-dioxene in the presence of a catalytic amount of a chloride of cobalt, iron, manganese, nickel, tin or zinc, wherein R$^4$ is lower alkyl and A is lower alkylene.

6. Process according to claim 5 wherein the process is carried out at a temperature of about 70° to 80° C. in the presence of a catalytic amount of zinc chloride.

7. Process according to claim 5 wherein the process is carried out at a temperature of about 90° to 95° C. in the presence of a catalytic amount of a chloride of tin.

* * * * *